United States Patent
Thomas et al.

(10) Patent No.: US 10,470,987 B2
(45) Date of Patent: Nov. 12, 2019

(54) PROCESS FOR STIMULATING HYALURONIC ACID SYNTHESIS

(71) Applicants: TOMCAT INTERNATIONAL LIMITED, London (GB); PRESIDENT AND FELLOWS OF HARVARD COLLEGE, Cambridge, MA (US)

(72) Inventors: Bertrand Thomas, New York, NY (US); Mathilde Thomas, New York, NY (US); David Sinclair, Chestnut Hill, MA (US)

(73) Assignees: TOMCAT INTERNATIONAL LIMITED, London (GB); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/578,262

(22) PCT Filed: Jun. 5, 2015

(86) PCT No.: PCT/IB2015/054257
§ 371 (c)(1),
(2) Date: Nov. 30, 2017

(87) PCT Pub. No.: WO2016/193791
PCT Pub. Date: Dec. 8, 2016

(65) Prior Publication Data
US 2018/0161256 A1 Jun. 14, 2018

(51) Int. Cl.
| | |
|---|---|
| *A61Q 19/08* | (2006.01) |
| *A61K 8/34* | (2006.01) |
| *A61K 8/73* | (2006.01) |
| *A61Q 19/00* | (2006.01) |
| *A61K 8/02* | (2006.01) |

(52) U.S. Cl.
CPC .............. *A61K 8/347* (2013.01); *A61K 8/022* (2013.01); *A61K 8/735* (2013.01); *A61Q 19/00* (2013.01); *A61Q 19/08* (2013.01); *A61K 2800/78* (2013.01); *A61K 2800/84* (2013.01); *A61K 2800/91* (2013.01); *A61K 2800/92* (2013.01)

(58) Field of Classification Search
CPC .... A61K 8/347; A61K 8/735; A61K 2800/92; A61K 2800/78; A61Q 19/00; A61Q 19/08
See application file for complete search history.

(56) References Cited

U.S. PATENT DOCUMENTS

| | | | |
|---|---|---|---|
| 6,147,121 A | 11/2000 | Breton et al. | |
| 6,572,882 B1* | 6/2003 | Vercauteren | A61K 8/375 424/451 |
| 2010/0310615 A1 | 12/2010 | Vercauteren | |
| 2014/0363502 A1* | 12/2014 | Sardi | A61K 31/05 424/451 |

FOREIGN PATENT DOCUMENTS

| | | |
|---|---|---|
| EP | 2 649 986 A2 | 10/2013 |
| FR | 2 766 176 A1 | 1/1999 |
| FR | 2 777 186 A1 | 10/1999 |
| WO | 99/03816 A1 | 1/1999 |
| WO | 2007/009790 A1 | 1/2007 |
| WO | 2008/072905 A | 6/2008 |
| WO | 2009/063440 A1 | 5/2009 |
| WO | 2012/116391 A1 | 9/2012 |
| WO | 2014210308 A1 | 12/2014 |

OTHER PUBLICATIONS

Farwick et al., title: Low Molecular Weight Hyaluronic Acid: Its Effects on Epidermal Gene Expression & Skin Ageing, SOFW Journal, English edition, published Nov. 2008 (Year: 2008).*
Ken Szulczyk: "Everything You Wanted to Know About Hyaluronic Acid", Mar. 6, 2014 (Mar. 6, 2014), XP002743996, Retrieved from the Internet <URL:http://szulczyk.blogspot.de/2014/03/everything-you-wanted-to-know-about.html> [retrieved on Sep. 3, 2015].
Bill Sardi: "Healthy Living into your Second Century; Bringing Youthfulness to Longevity", Dec. 31, 2009 (Dec. 31, 2009), XP002743997, Retrieved from the Internet <URL:http://www.longevinexadvantage.com/pdf/longevAdvntg_healthyLiving.pdf> [retrieved on Sep. 3, 2015].
International Search Report, dated Oct. 7, 2015, from corresponding PCT/IB2015/054257 application.
Saadat, E., et al., "Hyaluronic Acid Based Micelle for Articular Delivery of Triamcinolone, Preparation, In Vitro and In Vivo Evaluation," International Journal of Pharmaceutics, vol. 489, 2015, pp. 218-225.
Umerska, A., et al., "Self-Assembled Hyaluronate/Protamin Polyelectrolyte Nanoplexes: Synthesis, Stability, Biocompatibility and Potential Use as Peptide Carriers," Journal of Biomedical Nanotechnology, 2014, 48 pages.
Back, J., et al., "Application of Hyaluronic Acid/Sodium Alginate-Based Microparticles to Prevent Tissue Adhesion in a Rabbit Model," Surg. Today, vol. 46, 2016, pp. 501-508.
Laffleur, F., et al., "Permeation Enhancement via Thiolation: In Vitro and Ex Vivo Evaluation of Hyaluronic Acid-Cysteine Ethyl Ester," Journal of Pharmaecutical Sciences, vol. 104, 2015, pp. 2153-2160.
Zhang, X., et al., "Improved Method for Synthesis of Cysteine Modified Hyaluronic Acid for In-Situ Hydrogel Formation," Chem Commun (Camb), vol. 51, No. 47, 2015, 10 pages.
Chastang, T., "Study of the Synthesis of Resveratrol and its Derivatives (Viniferines) by Suspensions of Vine Cells and Optimization of Production in Bioreactor," HAL, 2014, 193 pages; with English translation.
Gertz, M., et al., "A Molecular Mechanism for Direct Sirtuin Activation by Resveratrol," PLOS One, vol. 7, Issue 11, 2012, pp. 1-12.
Aaltonen, K., et al., "Determination of the Unsaturated Disaccharides of Hyaluronic Acid in Equine Synovial Fluid by High-Performance Liquid Chromatography and Fluorescene Detection," Acta Veterinaria Scandinavica, vol. 57, No. 12 2015, pp. 1-4.

(Continued)

*Primary Examiner* — Yanzhi Zhang
(74) *Attorney, Agent, or Firm* — Young & Thompson

(57) ABSTRACT

Compositions allowing the stimulation of hyaluronic acid synthesis via an increase in has-2 expression and their use in the treatment of conditions related to a decrease in hyaluronic acid synthesis.

3 Claims, 1 Drawing Sheet

(56) References Cited

OTHER PUBLICATIONS

Figure 1:
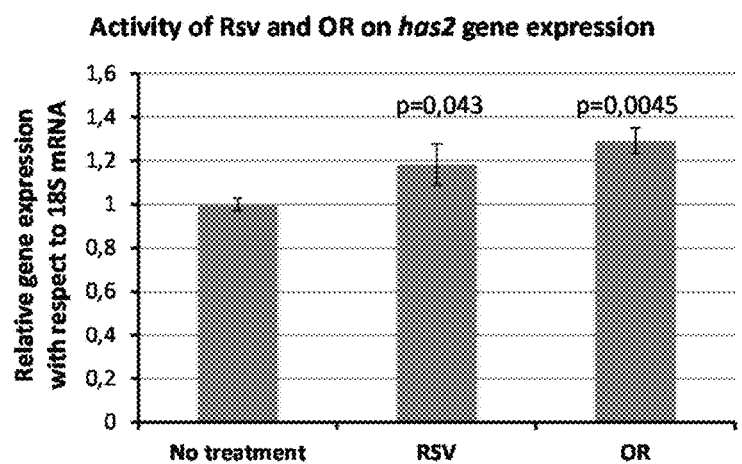

Wood, J., et al., "Sirtuin Activators Mimic Caloric Restriction and Delay Ageing in Metazoans," Letters to Nature, vol. 430, 2004, pp. 686-689.
Howitz, K., et al., "Small Molecule Activators of Sirtuins Extend *Saccharomyces cerevisiae* Lifespan," Letters to Nature, vol. 425, 2003, pp. 191-196.
Camenisch, T., et al., "Disruption of Hyaluronan Synthase-2 Abrogates Normal Cardiac Morphogenesis and Hyaluronan-Mediated Transformation of Epithelium to Mesenchyme," J. Clin. Invest, vol. 106, 2000, pp. 349-360.
Kogan, G., et al., "Hyaluronic Acid: A Natural Biopolymer with a Broad Range of Biomedical and Industrial Applications," Biotechnol Lett, vol. 29, 2007, pp. 17-25.
Written Opinion issued in Application No. PCT/IB2015/054257, dated Dec. 5, 2017.

\* cited by examiner

PROCESS FOR STIMULATING HYALURONIC ACID SYNTHESIS

The present invention relates to a new process for stimulating hyaluronic acid synthesis, to compositions stimulating hyaluronic acid synthesis, and to their use in the fields of cosmetology, human and veterinary medicine and also in the food industry.

Hyaluronic acid is an ubiquitous natural polysaccharide which is formed by disaccharide repeating units of D-glucuronic acid and N-acetyl-D-glucosamine, bonded to each other by alternating β-1,4 and β-1,3 glycosidic linkages. It is widely distributed in various body tissues, such as connective, epithelial and neural tissues. It is thus adapted to biomedical applications targeting these tissues and is for example used to treat knee osteoarthritis. Hyaluronic acid is often used as intra-articular injections, because it would protect joints by increasing the viscosity of synovial fluid by making the cartilage more elastic.

Hyaluronic acid is naturally present in the skin where it plays an important role in hydratation and in the biomechanical properties of the skin. However, hyaluronic acid decreases in quantity and quality with age, causing a drying out of the skin and a decrease of its biomechanical properties, thus the appearance of wrinkles.

Hyaluronic acid is metabolically extremely active. The degradation of hyaluronic acid is first catalyzed by hyaluronidase. On the other hand, polymeric hyaluronic acid can be non-enzymatically degraded by free radicals.

The enzymes responsible for the hyaluronic acid synthesis are hyaluronane synthases HAS-1, HAS-2, and HAS-3. HAS-2 seems to play an essential role during development since the deletion of has-2 gene in a mouse is lethal at mid-gestation because of numerous cardiovascular malformations (Camenisch T D. et al., *J. Clin. Invest.*, 2000, 106(3): 349-60).

Hyaluronic acid is widely used in dermatology and in dermo-esthetics to treat aging signs. It is injected into the dermis to fill wrinkles as described in document Kogan, G. et al. (*Biotechno. Letter*, 2007, 29: 17-25). It has the advantage of being resorbable in the case of an improper injection and without side effect, even in the case of a treatment over several years. The treatment requires repeated injections at regular intervals, generally from 6 to 12 months, in order to maintain a filling action.

Resveratrol (3,5,4'-trihydroxystilbene) is in two isomeric forms, the cis and trans forms, and is in a monomeric form, or an oligomeric form containing several monomeric units.

The study of resveratrol's properties has highlighted multiple biological activities of interest. Resveratrol is a strong antioxidant and anti-inflammatory agent with cardiovascular and anticarcinogenic effects. One of its most promising actions is its anti-aging action because of its capacity to increase the activity of sirtuins, a family of longevity genes capable of extending the lifespan of cells and organisms (Sinclair D. et al., *Nature*, 2003, 425: 191-196; Steegborn C. et al., *PLoS One*, 2012, 7(11); Wood J. G. et al. *Nature* 430: 686-689).

Studies conducted by the applicant have demonstrated that resveratrol extracted from vine shoots naturally enhances skin firmness and youth.

Resveratrol from vine shoots, overactivated by alkylation is the object of international application WO 9903816. In this application, the inventors describe extraction methods resulting in monomeric and/or oligomeric resveratrol-enriched extracts, using phenolic function-protecting groups, more particularly ester groups, enabling to provide monomeric and oligomeric resveratrols with air and light stability and to make them oil-soluble. These protecting groups can be removed under determined conditions, which enable resveratrol properties to be exploited in a controlled way.

International application WO2009/063440 relates in particular to resveratrol-Oleyl, alkylated resveratrol stabilized by admixing a fatty acid chain that is capable of hindering the formation of glycated molecules. Resveratrol-Oleyl not only protects against carbonylation (a type of protein modification that occurs during aging) but also provides increased skin bioavailability thanks to its stabilization and solubilization by oleic acid.

To date, different studies have reported associations between the effects of resveratrol and hyaluronic acid.

International application WO2014210308 describes the use of resveratrol in association with high molecular weight hyaluronic acid for wound healing.

International application WO2012116391 describes a cosmetic or pharmaceutical formulation comprising a hyaluronate cross linked polymer and one or more compounds selected from a group comprising in particular resveratrol or one derivative thereof. These compositions stimulate the collagen formation in dermis and regulate cellular turnover. They can be used against dermis oxidative damages and pigmentation problems.

Application US2014363502 relates to resveratrol containing compositions and their use to modulate, more significantly than resveratrol alone, the expression of some genes involved in particular in aging. It describes in particular a combination of resveratrol and hyaluronic acid. According to this document, the most significant effect of the compositions according to the invention would be ascribed to a better stability of combined resveratrol in comparison with resveratrol alone. These compositions can be useful in the treatment and prevention of cancers, and age-related diseases, in particular macular degeneration.

Despite the existence of numerous cosmetic and pharmaceutical compositions containing resveratrol alone or in association with hyaluronic acid, there is a need for compositions able to stimulate hyaluronic acid production in view of restoring or maintaining biological and biomechanical properties of tissues and having improved properties for treating dysfunctions related to a deficiency in hyaluronic acid synthesis, in particular for treating and protecting tissues containing hyaluronic acid (skin, cartilage . . . ), even more particularly for treating, slowing and preventing skin aging.

Herein, the inventors have discovered a surprising connection between resveratrol and hyaluronic acid synthesis. Indeed, the inventors have demonstrated for the first time an effect of resveratrol on hyaluronic acid production in a mammalian cell or tissue. Moreover, they have shown that there is a synergistic effect of resveratrol and hyaluronic acid on hyaluronic acid synthesis.

Thus, one embodiment of the present invention is the use of a composition comprising an efficient amount of resveratrol or its analogs and derivatives to stimulate hyaluronic acid synthesis. More precisely, it relates to the use of such a composition to modify has-2 expression.

Another embodiment of the invention is to provide a process for stimulating hyaluronic acid production in vitro or in vivo comprising a step of contacting mammal cells or tissue, in particular fibroblasts, keratinocytes or epithelial cells of cornea, with an appropriate amount of resveratrol.

For the purposes of the present invention, by mammal, it is meant a human or non-human mammal.

According to the invention resveratrol means resveratrol being monomers and oligomers and derivatives thereof in particular cis-resveratrol, trans-resveratrol, ε-viniferin, resveratrol esters, being monomers and oligomers, in particular methylated or acetylated resveratrol and the monomers including at least one ester group of the formula —O—CO-A, and the oligomers being formed by monomeric units linked by carbon-carbon, or ether bonds, and/or by monomers cross linked by —O—CO—R—CO—O— groups, -A representing an alkyl radical of at least two carbon atoms, which radical is linear or branched, saturated or unsaturated, an aryl, aralkyl or aralkylene radical, and —R representing an alkylene radical of 0 to 10 carbon atoms, which is saturated or unsaturated, and/or 1 arylene radical having 1 to 3 rings and/or a heterocyclic radical, and diastereoisomers of these units. Such derivatives are described in patent FR2766176.

Resveratrol monomers and/or oligomers can be synthesized chemically or obtained from different plant sources selected from the following group: Vitaceae, Umbelliferae, Myrtaceae, Dipterocarpaceae, Cyperaceae, Gnetaceae, legumes, Gramineae, Sericeae, Haemodoraceae, Musaceae, Polygonaceae, Pinaceae, Cupressaceae, Cesalpiniaceae, Poaceae, and Solanaceae.

In an advantageous embodiment of the invention, resveratrol is used as a resveratrol-rich fraction from vine (OR).

Advantageously, resveratrol monomers and/or oligomers obtained by extraction using water and/or an organic solvent are used, from grape stalks according to techniques known to those skilled in the art, in particular those described in literature.

Resveratrol can also be obtained by the use of genetically modified microorganisms, from animal tissues or by bioproduction from plants, in particular from suspensions of vine cells (Etude de la synthèse du resveratrol et de ses dérivés par des suspensions de cellules de vigne et optimisation de la production en bioréacteur, Thomas Chastang 23 juillet 2014 https://tel.archives-ouvertes.fr/tel-01037913/document).

According to a particularly advantageous embodiment, the composition further comprises as an active principle hyaluronic acid or a salt thereof.

In accordance with the present invention, the term "hyaluronic acid" (or hyaluronane) refers to a linear polymer consisting of the repetition of D-glucuronic acid disaccharides and N-acetyl-D-glucosamine, linked to each other through alternate glycosidic β-1,4 and β-1,3 ([-β(1,4)-GlcUA-β(1,3)-GlcNAc-]n). Hyaluronic acid is widely commercially available or can be prepared or extracted by any technique known to those skilled in the art. This polymer can be natural or synthetic.

In accordance with the present invention, the term "hyaluronic acid" (or hyaluronane) also refers to homologs, analogs, derivatives, complexes, esters, fragments, and subunits of hyaluronic acid, Hyaluronic acid occurs naturally as unsaturated disaccharides (*Acta Vet Scand.* 2015 Mar. 4; 57(1):12) and may also be chemically modified to improve its absorption characteristics such as modifications on the hydroxyl groups through an ether bond to obtain cysteine-hyaluronic acid conjugate (*Chem Commun (Camb).* 2015 51(47):9662-5) or the formation of I-cysteine ethyl ether (C) via an amide bond (*J Pharm Sci.* 2015 Apr. 21. doi: 10.1002/jps.24456).

The composition may further comprise as an active principle hyaluronic acid covalently attached to resveratrol monomers or oligomers via carbon-carbon, or ether or ester bonds, such as modifications on the hydroxyl groups of hyaluronic acid. In an advantageous embodiment of the invention, hyaluronic acid is covalently attached to resveratrol monomers or oligomers via carbon-carbon, or ether or ester bonds at the C6 position of hyaluronic acid. Hyaluronic acid and resveratrol may also be delivered in carriers including liposomes, skin penetrating peptides, polyelectrolyte complex nanocarrier complex (*Biomed Nanotechnol.* 2014 December; 10(12):3658-73) sodium alginate-based microparticles (*Surg Today.* 2015 May 20), poly-I-lysine, or a triamcinolone loaded polymeric micelle (Int J Pharm. 2015 May 5; 489(1-2):218-225)

In accordance with the invention, the mean molecular weight of hyaluronic acid used varies as a function of the administration mode. Thus, for the administration by topical route, the mean molecular weight of hyaluronic acid is advantageously lower than 100 kDa, even more advantageously between 5 kDa and 100 kDa, even more advantageously between 50 kDa and 100 kDa. For the administration by oral or parenteral route, high molecular weight hyaluronic acid can be used.

According to a particular embodiment, the composition is a topical use cosmetic composition comprising an efficient amount of resveratrol or of a derivative thereof alone or combined with an efficient amount of hyaluronic acid and further at least one cosmetically acceptable excipient selected from oils, waxes, emollients, solvents, pigments, colorants, polymers, surfactants, rheology agents, fragrances, electrolytes, pH adjustors, anti-oxidant agents and preservatives.

Thus in accordance with the invention, the compositions may contain either resveratrol alone, or at least one of a derivative thereof alone, or resveratrol and at least one of a derivative thereof, or resveratrol alone associated with hyaluronic acid, or at least one of a derivative thereof associated with hyaluronic acid or resveratrol and at least one of a derivative thereof associated with hyaluronic acid. For the purposes of the present invention, by hyaluronic acid salt, it is meant in particular sodium and potassium salts. Other known hyaluronic salts include magnesium, aluminium, or ammonium salts.

According to a particularly preferred embodiment, the cosmetic composition is a skin care or make-up product and is in the form, for example of a gel, cream, lotion, milk, oil, salve, foam, serum, ointment or even a hydrogel, in particular a mask, or is in the form of a stick, for example a lipstick or even a patch.

According yet another aspect, the invention is directed to a cosmetic care method, characterized in that it comprises topically applying on the skin an efficient amount of a cosmetic composition according to the invention, in particular for maintaining or restoring skin hydratation and skin biomechanical properties and/or for preventing or delaying the appearance of skin aging signs, in particular the appearance of wrinkles and the loss of skin firmness or slowdown the effects thereof.

According to a particularly advantageous alternative of the invention, this cosmetic care method is characterized in that a cosmetic care intended to prevent, slowdown or correct skin aging, in particular intended to firm up skin and/or promote wrinkle attenuation and resorption is made.

According to another aspect of the invention, said composition can be in the form of a pharmaceutical composition for a topical application (this is called a dermatological composition) or for an oral or parenteral administration. It can also be in the form of a food composition, in particular a food supplement. All these forms contain, in association with a physiological acceptable carrier, an efficient amount of resveratrol alone or combined with an efficient amount of hyaluronic acid.

All the compositions according to the invention, whether cosmetic, pharmaceutical or food compositions, can further contain other active principles, in particular products having an antioxidant effect such as 6-carotene, vitamin E or vitamin C, Oligo-Proanthocyanidines (OPC), retinol and mixtures thereof.

Resveratrol and hyaluronic acid amounts will be determined by those skilled in the art in the light of their general knowledge.

By way of example, for the administration by the oral route, the composition can be formulated such that resveratrol is administered at a dose between 10 mg/d and 5 g/d; when associated with hyaluronic acid, it is present at a concentration enabling a dose between 10 mg/d and 5 g/d to be administered. These doses can be administered in one or several daily doses. For the topical administration, the cosmetic or dermatological composition can be formulated such that resveratrol represents 0.01 to 1 weight % of the composition and hyaluronic acid 0 to 0.4 weight % of the composition. The administration can be made in one or more applications. For the parenteral route, the composition can be formulated as an aqueous solution comprising between 1 µg/ml and 100 mg/ml resveratrol and between 0 µg/ml and 100 mg/ml hyaluronic acid. These doses can be administrated one or several times a day.

For the topical administration, the pharmaceutical compositions can have any commonly used forms such as for example a gel, cream, lotion, milk, oil, salve, foam, serum, ointment, hydrogel or patch.

For the oral administration, the pharmaceutical or food compositions can have any commonly used form and are preferably in the form of tablets, capsules, powders, granules, lyophilisates, solutes, suspensions, syrups, drinks, pastes, chewing gums, or sweets.

When the administration is of the parenteral type, the composition according to the present invention is preferably formulated as an injectable sterile solution. It can also be in the form of a lyophilized powder, the solvent being added extemporaneously or upon use.

The pharmaceutical, veterinary or food compositions according to the invention are more particularly suitable for treating or preventing osteoarthritis and skin aging. They can further be used for preventing and/or treating diseases affecting mucosae of the airways, such as asthma, respiratory allergies, respiratory distress syndrome, or digestive disorders, in particular gastro-enteritis, ischemic necroses and gastro-intestinal mucous membrane ulcerations.

The compositions according to the invention can be intended to a use in the field of treatments of eye disorders, in particular keratitis sicca, cornea injuries and keratopathies.

Thus, one object of the present invention is also to provide a method for therapeutically treating dysfunctions related to a decrease in hyaluronic acid, said method comprising administrating to a subject in need thereof an efficient amount of resveratrol alone or associated with hyaluronic acid.

One object of the invention is also to provide a composition including, in a physiologically acceptable medium:
i) resveratrol being monomers or oligomers or derivatives thereof in particular cis-resveratrol, trans-resveratrol, ε-viniferin, resveratrol esters, being monomers and oligomers, in particular methylated and acetylated resveratrol and the monomers including at least one ester group of the formula —O—CO-A, and the oligomers being formed by monomeric units joined by carbon-carbon, or ether bonds, and/or by monomers cross-linked by —O—CO—R—CO—O— groups, -A representing an alkyl radical of at least two carbon atoms, being linear or branched, saturated or unsaturated, an aryl, aralkyl, or aralkylene radical, and —R representing an alkylene radical from 0 to 10 carbon atoms, being saturated or unsaturated and/or 1 arylene radical having 1 to 3 rings and/or a heterocyclic radical, and diastereoisomers of these units and
ii) hyaluronic acid or a salt thereof having a mean molecular weight between 50 kDa and 100 kDa, advantageously equal to 50 kDa,
said hyaluronic acid being covalently attached to resveratrol being monomers or oligomers or derivatives thereof in particular cis-resveratrol, trans-resveratrol, ε-viniferin, via carbon-carbon, or ether or ester bonds at hydroxyl positions of hyaluronic acid.

Figure 2:
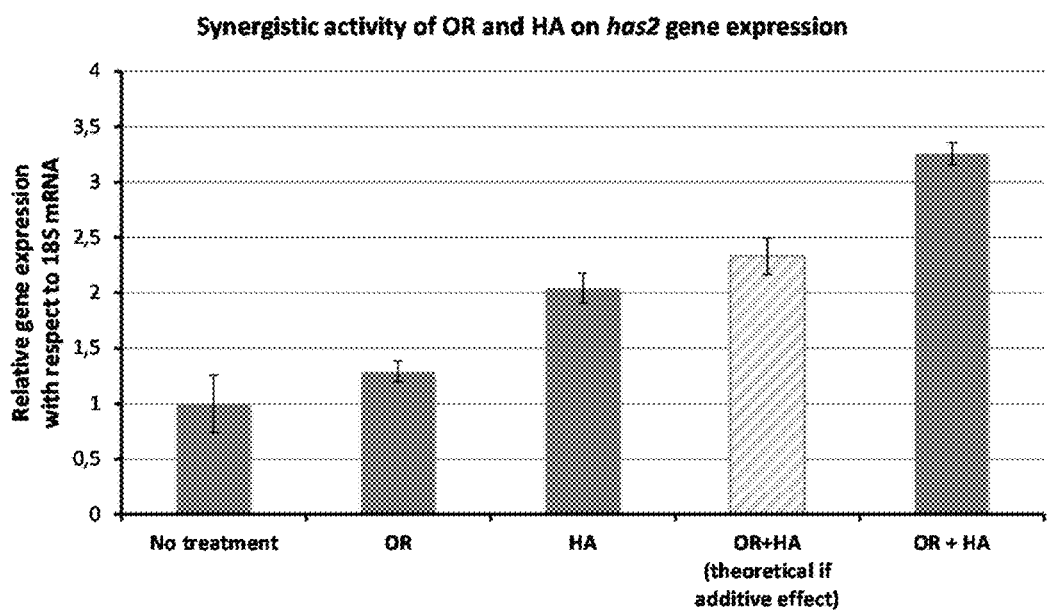

The invention is illustrated by the examples 1 and 2 and FIGS. 1 and 2 that follow.

FIG. 1 illustrates the effect of resveratrol (RSV) and resveratrol oligomers (OR) on the has-2 expression observed after 6 hours incubation. "Untreated" corresponds to incubated fibroblasts in the absence of products to be tested. The results are expressed as the average±standard deviation of four samples per treatment.

FIG. 2 illustrates the effect of resveratrol oligomers (OR), hyaluronic acid (HA) and the combination of resveratrol oligomers and hyaluronic acid (OR+HA) on has-2 expression observed after 23 hours incubation. Hatched column OR+HA corresponds to the theoretical value if there was an additive effect between OR and HA. Black column OR+HA corresponds to the synergistic effect measured. "Untreated" corresponds to fibroblasts incubated in the absence of products to be tested. Results are expressed as the average f standard deviation of four samples per treatment.

EXAMPLE 1: EFFECT OF RESVERATROL AND RESVERATROL OLIGOMERS ON HAS-2 EXPRESSION IN FIBROBLASTS 1.1. Operating Mode Human skin fibroblast cells are spread in DMEM medium containing 10% of fetal bovine serum (FBS) and antibiotics (penicillin/streptomycin) and incubated until a 90% confluence is reached. The medium is removed and replaced by fresh medium comprising resveratrol (RSV) or resveratrol oligomers (OR) respectively. Table 1 below indicates the different conditions tested and concentrations used.

TABLE 1

| No | Type of treatment |
| --- | --- |
| 1 | Untreated |
| 2 | Resveratrol (RSV) 2 µM |
| 3 | Resveratrol oligomers (OR) 2 µM |

Human skin fibroblast cells are incubated for 6 hours at 37° C. under 5% $CO_2$. The ARN extraction is made by using the ARN Omega extraction kit. 1 µg of ARN is used and retranscribed into complementary DNA using the ADNc Bio-Rad iScript™ synthesis kit followed by a real time quantitative PCR quantification. The PCR reactions have been carried out using Fast-Start™ DNA Master SYBR Green I real-time PCR kit (Roche Molecular Biochemicals).

Each PCR has been carried out in a final volume of 20 μl containing 10 μl of SYBR Green mix 2× (Fast start DNA master SYBR green+Taq DNA polymerase), 2 μl of 10 μM primer mixture (finally 1 μM) and 8 μl of ADNc solution (50 ng). The primers used are described in table 2 below.

TABLE 2

| Oligo Name | Sequence | Description |
|---|---|---|
| f-qPCR-18S | gag act ctg gca tgc taa cta g | 18S rRNA |
| r-qPCR-18S | gga cat cta aga gca tca cag | 18S rRNA |
| f-qPCR-hHAS2 | CTCTTTTGGACTGTATGGTGCC | Hyaluronan synthase 2 |
| r-qPCR-hHAS2 | AGGGTAGGTTAGCCTTTTCACA | Hyaluronan synthase 2 |

2.2. Results

The results are presented in FIG. 1.

These results show that after 6 h incubation, resveratrol and oligo-resveratrol (OR) significantly induce has-2 expression by fibroblasts by a factor 1.18 (+18%; p<0.043) and a factor 1.29 (+29%; p<0.0045) respectively. Under these conditions, resveratrol and resveratrol oligomers have a substantially equal activity.

EXAMPLE 2: EFFECT OF RESVERATROL OLIGOMERS ALONE OR ASSOCIATED WITH HYALURONIC ACID ON HAS-2 EXPRESSION IN FIBROBLASTS 2.1. Operating Mode Human skin fibroblast cells are spread in DMEM medium containing 10% fetal bovine serum (FBS) and antibiotics (penicillin/streptomycin) and incubated until a 60% confluence is reached. The rest of the operating mode is identical to that described hereinbefore except that the incubation time is 23 hours. Table 3 below indicates different conditions tested and concentrations used.

TABLE 3

| No | Type of treatment |
|---|---|
| 1 | Untreated |
| 3 | Resveratrol oligomers (OR) 2 μM |
| 4 | HA 150 μg/ml |
| 6 | HA 150 μg/ml + OR 2 μM |

2.2. Results

The results are presented in FIG. 2.

These results show that resveratrol oligomers (OR) increase by a factor 1.3 (+29%) has-2 expression by fibroblasts. has-2 expression is increased by a factor 2 (+104%) by HA. Thanks to a OR and HA mixture, a simple additive effect of both activities would enable an induction factor of 2.3 (+133%) (hatched/hashed bar in the graph) to be theoretically obtained. In practice, when fibroblasts are treated with a HA/OR mixture for 23 hours, a significant increase in the has-2 expression corresponding to a factor of 3.25 (+226%) is observed. Thus, the effect of HA+OR is synergistic in comparison with the treatment with HA alone on the one hand and OR alone on the other hand.

Thus, these results show for the first time that resveratrol and the resveratrol oligomer increase the expression of has-2 gene, thus stimulating hyaluronic acid production by human fibroblasts. Moreover, these results show that resveratrol acts in synergy with hyaluronic acid, the combination of these compounds significantly increasing has-2 expression.

These results confirm that the composition according to the invention can be used as a cosmetic, pharmaceutical and/or food composition for treating dysfunctions and/or conditions responsive to an increase in hyaluronic acid synthesis.

The invention claimed is:

1. A process for stimulating hyaluronic acid in vitro or in vivo production by a mammal cell or tissue, comprising administering a composition comprising consisting of a combination of an efficient amount of resveratrol oligomers and an efficient amount of hyaluronic acid or a salt thereof as solely active principles and wherein the mammal cell or tissue are fibroblasts, keratinocytes or epithelial cells of cornea.

2. A process according to claim 1, wherein the monomeric units forming the oligomers of resveratrol are cis-resveratrol, trans-resveratrol, ε-viniferin, resveratrol esters, methylated or acetylated resveratrol and the monomers including at least one ester group of the formula —O—CO-A, and the oligomers being formed by monomeric units joined by carbon-carbon, or ether bonds, and/or monomers cross-linked by —O—CO—R—CO—O— group, with -A representing an alkyl radical with at least two carbon atoms, being linear or branched, saturated or unsaturated, an aryl, aralkyl or aralkylene radical, and —R representing an alkylene radical with 0 to 10 carbon atoms, being saturated or unsaturated, and/or 1 arylene radical having 1 to 3 rings and/or a heterocyclic radical, and diastereomers of these units.

3. A process according to claim 1, wherein the hyaluronic acid or a salt thereof has a mean molecular weight between 50 kDa and 100 kDa.

* * * * *